United States Patent
McIntyre et al.

[11] Patent Number: 5,976,192
[45] Date of Patent: *Nov. 2, 1999

[54] METHOD OF FORMING AN EXTERNALLY SUPPORTED TAPE REINFORCED VASCULAR GRAFT

[75] Inventors: John McIntyre, Vista; Donald Shannon, Mission Viejo; Chris Kuo, Orange; Chris McCollam; Robert Peterson, both of Irvine, all of Calif.

[73] Assignee: Baxter International Inc., Deerfield, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/762,113

[22] Filed: Dec. 10, 1996

Related U.S. Application Data

[63] Continuation of application No. 08/482,177, Jun. 7, 1995, abandoned.

[51] Int. Cl.⁶ ........................................................ A61F 2/06
[52] U.S. Cl. .................... 623/901; 623/1; 600/36; 138/144
[58] Field of Search ............................. 623/1, 12, 901; 600/36; 138/118.1, 122, 144

[56] References Cited

U.S. PATENT DOCUMENTS

| | | | |
|---|---|---|---|
| 3,105,492 | 10/1963 | Jeckel | 623/1 |
| 3,479,670 | 11/1969 | Medell | 623/1 |
| 3,490,975 | 1/1970 | Lightwood et al. | 623/1 |
| 4,306,318 | 12/1981 | Mano et al. | 623/12 |
| 4,550,447 | 11/1985 | Seilek, Jr. et al. | 623/1 |
| 4,629,458 | 12/1986 | Pinchuk | 623/1 |
| 4,743,252 | 5/1988 | Martin, Jr. et al. | 623/1 |
| 4,798,606 | 1/1989 | Pinchuk | 623/1 |
| 4,871,365 | 10/1989 | Dumican | 623/11 |
| 4,954,126 | 9/1990 | Wallsten | 600/36 |
| 4,986,831 | 1/1991 | King et al. | 623/1 |
| 4,990,158 | 2/1991 | Kaplan et al. | 623/1 |
| 5,015,253 | 5/1991 | MacGregor | 623/1 |
| 5,061,275 | 10/1991 | Wallsten et al. | 623/1 |
| 5,084,065 | 1/1992 | Weldon et al. | 623/1 |
| 5,116,360 | 5/1992 | Pinchuk et al. | 623/1 |
| 5,171,262 | 12/1992 | MacGregor | 623/1 |
| 5,178,630 | 1/1993 | Schmitt | 623/1 |
| 5,192,311 | 3/1993 | King et al. | 623/1 |
| 5,246,452 | 9/1993 | Sinnott | 623/1 |
| 5,282,846 | 2/1994 | Schmitt | 623/1 |
| 5,282,860 | 2/1994 | Matsuno et al. | 623/12 |
| 5,290,305 | 3/1994 | Inoue | 606/191 |
| 5,304,200 | 4/1994 | Spaulding | 606/198 |
| 5,306,286 | 4/1994 | Stack et al. | 606/198 |
| 5,628,782 | 5/1997 | Myers et al. | 623/12 |

FOREIGN PATENT DOCUMENTS

| | | | |
|---|---|---|---|
| 177167 | 9/1984 | European Pat. Off. | |
| 0146794 | 7/1985 | European Pat. Off. | 623/12 |
| 232543 | 12/1985 | European Pat. Off. | |
| 293090 | 4/1987 | European Pat. Off. | |
| 0587461 | 3/1994 | European Pat. Off. | |
| 699424 | 6/1994 | European Pat. Off. | |
| 0022792 | 6/1972 | Japan | 623/1 |
| 1008193 | 10/1965 | United Kingdom . | |
| 2033233 | 5/1980 | United Kingdom . | |
| 2189150 | 10/1987 | United Kingdom . | |
| WO 80/02641 | 12/1980 | WIPO . | |
| WO 83/03349 | 10/1983 | WIPO . | |
| WO 87/05796 | 10/1987 | WIPO . | |
| 8800813 | 2/1988 | WIPO | 623/1 |
| WO 92/16166 | 10/1992 | WIPO . | |

*Primary Examiner*—Bruce E. Snow
*Attorney, Agent, or Firm*—Bruce M. Canter; Guy L. Cumberbatch; Peter Jon Gluck

[57] ABSTRACT

An externally supported, tape-reinforced tubular prosthetic graft and method of manufacturing therefore. The graft comprises a tubular base graft formed of expanded, sintered fluoropolymer material, a strip of reinforcement tape helically wrapped about the outer surface of the tubular base graft and attached thereto, and, an external support member helically wrapped around the outer surface of the reinforcement tape and attached thereto. The helical pitch of the reinforcement tape is different from the helical pitch of the external support member. Preferably, the helical pitch of the reinforcement tape is in a direction which is opposite the direction of the external support member.

34 Claims, 1 Drawing Sheet

METHOD OF FORMING AN EXTERNALLY SUPPORTED TAPE REINFORCED VASCULAR GRAFT

RELATED CASES

This is a continuation of Ser. No. 08/482,177, entitled "EXTERNALLY SUPPORTED TAPE REINFORCED VASCULAR GRAFT", filed Jun. 7, 1995, now abandoned.

FIELD OF THE INVENTION

The present invention relates generally to prosthetic vascular grafts, and more particularly to a tubular, tape-reinforced externally supported vascular graft formed of a fluoropolymer such as polytetrafluoroethylene (PTFE), and methods of manufacture therefore.

BACKGROUND OF THE INVENTION

Fluoropolymers, such as PTFE have been heretofore used for the manufacture of various types of prosthetic vascular grafts. Among these are various vascular grafts having tubular configurations so that they may be utilized to replace an excised segment of blood vessel.

The tubular prosthetic vascular grafts have traditionally been implanted, by open surgical techniques, whereby a diseased or damaged segment of blood vessel is surgically excised and removed, and the tubular bioprosthetic graft is then anastomosed into the host blood vessel as a replacement for the previously removed segment thereof. Alternatively, such tubular prosthetic vascular grafts have also been used as bypass grafts wherein opposite ends of the graft are sutured to a host blood vessel so as to form a bypass conduit around a diseased, injured or occluded segment of the host vessel.

More recently, methods have been developed for endovascular implantation of tubular prosthetic vascular grafts. Such endovascular implantation initially involves translumenal delivery of the graft, in a compacted state, through a catheter or other delivery apparatus. Thereafter, the graft undergoes in situ expansion and affixation at its intended site of implantation within the host blood vessel. An affixation apparatus is typically utilized to affix the opposite ends of the tubular graft to the surrounding blood vessel wall. In this regard, the endovascularly implanted tubular graft may be utilized to repair an aneurismic segment of a host blood vessel, without requiring open surgical dissection of the host blood vessel.

In general, many of the tubular prosthetic vascular grafts of the prior art have been formed of extruded, porous PTFE tubes. In some of the tubular grafts of the prior art a tape, formed of PTFE film is wrapped about and laminated to the outer surface of a tubular base graft to provide reinforcement and additional burst strength. Also, some of the prior tubular prosthetic vascular grafts have included external support member(s), such as a PTFE beading, bonded or laminated to the outer surface of the tubular graft to prevent the graft from becoming compressed or kinked during implantation. These externally supported tubular vascular grafts have proven to be particularly useful for replacing segments of blood vessel which pass through, or over, joints or other regions of the body which undergo frequent articulation or movement.

One commercially available, externally-supported, tubular vascular graft is formed of a regular walled PTFE tube having a PTFE filament helically wrapped around, and bonded to, the outer surface of the PTFE tube. (IMPRA Flex™ Graft, IMPRA, Inc., Tempe, Ariz.)

One other commercially available, externally-supported, tubular vascular graft comprises a regular walled, PTFE tube which has PTFE reinforcement tape helically wrapped around, and bonded to, the outer surface of the PTFE tube and individual rings of Fluorinated Ethylene Propylene (FEP) rings disposed around, and bonded to, the outer surface of the reinforcement tape. (FEP ringed ePTFE vascular graft, W. L. Gore & Associates, Inc., Flagstaff, Ariz.)

When surgically implanting the externally-supported tubular vascular grafts of the prior art, it is typical for the surgeon to peel the support filament or support ring(s) away from the opposite ends of the tubular graft to facilitate anastomosis of the ends of the graft to the host blood vessel. However, such peeling away of the external support filament or ring(s) may, in at least some cases, also result in some peeling or fraying of any reinforcement tape from the adjacent end portions of the tubular graft. Such fraying or peeling of the reinforcement tape concurrently with removal of the external support member(s) is undesirable.

Accordingly, there remains a need in the art for the development of new externally-supported, tape-reinforced, tubular vascular grafts which are constructed to permit an external support member (e.g., a PTFE filament) to be peeled away from the end regions of the graft, without causing concurrent peeling or fraying of the underlying reinforcement tape from the tubular base graft.

SUMMARY OF THE INVENTION

The invention comprises an externally-supported, tape-reinforced, tubular prosthetic graft which comprises; a tubular base graft formed of expanded, sintered fluoropolymer (e.g. PTFE) material; a strip of reinforcement tape helically wrapped around and bonded to the outer surface of the tubular base graft, in a first helical pitch (i.e., configuration or direction); and, an external support member (e.g., PTFE beading) helically wrapped around and bonded to the outer surface of the reinforcement tape, in a second helical pitch (i.e., configuration or direction) which is different from said first helical pitch. In the preferred embodiment, the second helical pitch of the external support member is in a direction which is opposite the direction of the first helical pitch of the reinforcement tape.

Further in accordance with the invention, the external support member may be formed of substantially non-elastic material which is capable of providing external configurational support to the tubular graft so as to prevent substantial indentation or kinking of the tubular graft when positioned in a region of a host body which undergoes bending or other movement which would be likely to indent or kink the tubular graft.

Still further in accordance with the invention, there is provided a method of manufacturing the externally-supported, tape-reinforced, tubular prosthetic grafts of the present invention, said method comprising the steps of (a) providing a tubular base graft formed of expanded, sintered fluoropolymer material; (b) providing at least one strip of reinforcement tape formed of expanded sintered fluoropolymer film; (c) wrapping said reinforcement tape helically around the outer surface of the tubular base graft in a first helical disposition (i.e., configuration or direction); (d) causing the helically wrapped reinforcement tape to become fused to the tubular base graft; (e) providing an external support member formed of substantially non-elastic beading; (f) helically wrapping the external support member around the outer surface of the helically-wrapped reinforcement tape, in a second helical disposition (i.e., configuration or direction) which differs from the first helical disposition of the reinforcement tape; and, (g) causing the helically wrapped external support member to become attached to the helically wrapped reinforcement tape.

Further objects and aspects of the invention will become apparent to those skilled in the art upon reading and understanding of the following detailed description and the accompanying drawings.

DETAILED DESCRIPTION OF THE PREFERRED EMBODIMENT

The following detailed description and the accompanying drawings to which it refers are provided for purposes of describing and illustrating the presently preferred embodiments of the invention only, and are not intended to limit the scope of the invention in any way.

Figure 1:
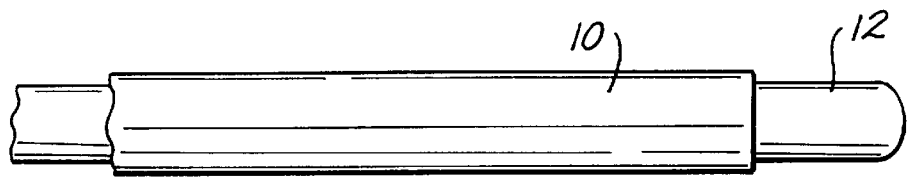
FIG. 1 is an elevational view of a first step in the manufacturing method of the present invention wherein a tubular base graft is positioned on a rigid mandrel.

FIG. 1 shows a first step in the method of the present invention wherein an extruded tubular fluoropolymer base graft 10 is disposed on a rod or mandrel 12.

The tubular base graft 10 will typically be manufactured of expanded, sintered PTFE in accordance with the following general methodology:

A. Preparation of the Tubular Base Graft i.) Preparation of Paste

The manufacture of the tubular base graft begins with the step of preparing a PTFE paste dispersion for subsequent extrusion. This PTFE paste dispersion may be prepared by known methodology whereby a fine, virgin PTFE powder (e.g., F-104 or F-103 Virgin PTFE Fine Powder, Dakin America, 20 Olympic Drive, Orangebury, N.Y. 10962) is blended with a liquid lubricant, such as odorless mineral spirits (e.g., Isopar®, Exxon Chemical Company, Houston, Tex. 77253-3272), to form a PTFE paste of the desired consistency.

ii.) Extrusion of Tube

The PTFE-lubricant blend dispersion is subsequently passed through a tubular extrusion dye to form a tubular extrudate.

iii.) Drying

The wet tubular extrudate is then subjected to a drying step whereby the liquid lubricant is removed. This drying step may be accomplished at room temperature or by placing the wet tubular extrudate in an oven maintained at an elevated temperature at or near the lubricant's dry point for a sufficient period of time to result in evaporation of substantially all of the liquid lubricant.

iv.) Expansion

Thereafter, the dried tubular extrudate is longitudinally expanded or longitudinally drawn at a temperature less than 327° C. and typically in the range of 250–326° C. This longitudinal expansion of the extrudate may be accomplished through the use of known methodology, and may be implemented by the use of a device known as a batch expander. Typically, the tubular extrudate is longitudinally expanded by an expansion ratio of more than two to one (2:1) (i.e., at least two (2) times its original length).

v.) Sintering

After the longitudinal expansion step has been completed, the tubular extrudate is subjected to a sintering step whereby the extrudate is heated to a temperature above the sintering temperature of PTFE (i.e., 350–370° C.) to effect amorphous-locking of the PTFE polymer. The methodology used to effect the sintering step, and the devices used to implement such methodology, are known in the art.

Completion of the sintering step marks the completion of the preparation of the expanded, sintered PTFE base graft 10.

Figure 2:
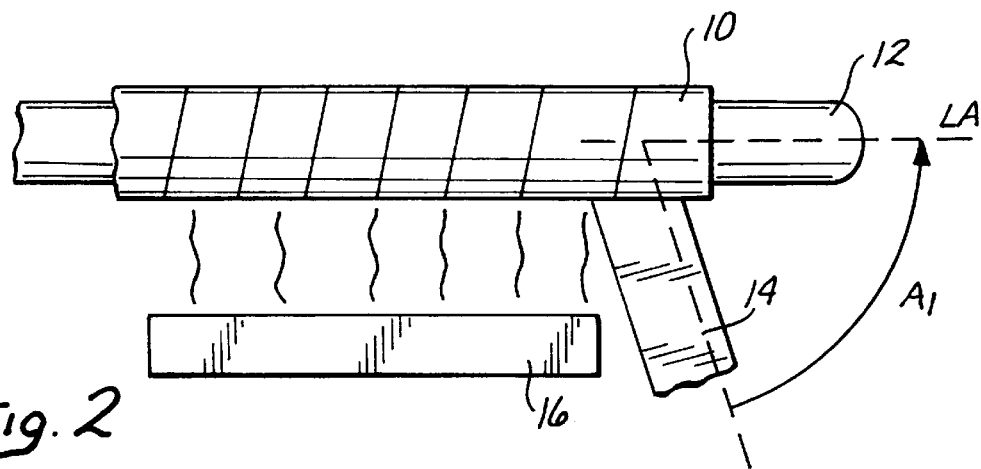
FIG. 2 is an elevational view showing of a second step of the manufacturing method of the present invention wherein a fluoropolymer film reinforcement tape is helically wrapped about, and heat laminated to, the outer surface of a tubular base graft.

FIG. 2 shows a second step in the method wherein a reinforcement tape 14 formed of material such as expanded sintered PTFE film is helically wrapped about the outer surface of the tubular base graft 10, and heat laminated thereto.

The reinforcement tape 14 may be manufactured by any suitable method, including the general method for manufacturing expanded PTFE reinforcement tape, as follows:

B. Preparation of Reinforcement Tape i.) Preparation of Paste Dispersion

The preparation of the expanded sintered PTFE reinforcement tape 14 includes the initial preparation of a PTFE paste dispersion. The PTFE paste dispersion prepared in this step may be prepared in the same manner as described hereabove for preparation of the PTFE paste dispersion used to form the tubular base graft.

ii.) Extrusion of Film

The PTFE paste dispersion is subsequently passed through the film extrusion dye to form a wet film extrudate. The wet film extrudate is taken up or wound upon a rotating core so as to form a roll of the wet film extrudate.

iii.) Calendaring

The wet film extrudate is subsequently unrolled and subjected to an initial cold (i.e., <100° C.) calendaring step by passing the film through at least one set of opposing stainless steel calendaring rollers having an adjustable gap thickness therebetween. The calendaring rollers are preferably maintained at a temperature between room temperature and 60° C. The width of the wet extrudate is held constant as it passes through these calendaring rollers. The thickness of the wet film extrudate is reduced to its desired final thickness (e.g., 0.004–0.005 inches) while the width of the film is maintained constant. It will be appreciated that, since the width of the film is maintained constant, the passage of the film through the calendaring machine will result in a longitudinal lengthening of the film. The amount of longitudinal lengthening will be a function of the decrease in film thickness which occurs as the film passes between the calendaring rollers.

One example of a commercially available calendaring machine useable for this purpose is the small Killion 2 Roll Stack, (Killion Extruders, Inc., Cedar Grove, N.J. 07009.)

iv) Drying

Thereafter, the wet film is subjected to a drying step. This drying step may be accomplished by permitting or causing the liquid lubricant to evaporate from the matrix of the film.

Such evaporation of the liquid lubricant may be facilitated by passing the film over a drum or roller which is maintained in an elevated temperature sufficient to cause the liquid lubricant to fully evaporate from the film matrix.

v) Expansion

Separately, or concurrently with the drying step the film is subjected to an expansion step. Such expansion step comprises expanding the PTFE film in at least one direction (e.g., longitudinally). Such expansion of the film serves to a) increase the porosity of the film, b) increase the strength of the film, and c) orient the PTFE fibrils in the direction of the axis of expansion.

This expansion step is typically carried out with some heating of the film during such expansion, but such heating does not exceed the crystalline melting point of the PTFE polymer.

vi) Sintering

After the drying step and expansion step have been completed, the film is subjected to a sintering step wherein the film is heated to a temperature above the melting point of PTFE to accomplish sintering or amorphous locking of the PTFE polymer. This sintering step may be carried out by passing the film over a drum or roller which is maintained at a high surface temperature (e.g., 350–420° C.) to cause the desired heating of the PTFE film above the melting point of the PTFE polymer for a sufficient period of time to effect the desired sintering of the film.

vii) Cutting the Film Into Strips

After the film has been dried, the film is cut into strips, each strip typically having a width of 0.25–0.50 inches, thereby creating strips of expanded, sintered PTFE reinforcement tape 14.

Thereafter, the strips of expanded sintered PTFE reinforcement tape 14 are helically wrapped about and laminated to the outer surface of the tubular base graft 10, in accordance with the following methodology:

C. Wrapping and Lamination of the Reinforcement Tape Onto the Tubular Base Graft The expanded sintered PTFE reinforcement tape 14 is helically wrapped onto the outer surface of the tubular base graft 10 by laying the reinforcement tape 14 onto the outer surface of the tubular base graft 10, at a desired angle $A_1$, relative to the longitudinal axis LA of the base graft, while the mandrel 12 and base graft 10 are rotated about such longitudinal axis LA. This results in helical wrapping of the reinforcement tape 14 onto the outer surface of the base graft 10, in a first helical configuration or pitch. The helical configuration or pitch is determined by the longitudinal spacing between the individual convolutions of the helix and is a function of the size and direction of angle $A_1$ which is the angle at which the tape 14 is wrapped relative to the longitudinal axis LA of the base graft.

The number of layers of tape 14 applied to the base graft 10 is variable for each size of graft. The number of layers of tape 14 depends on the desired mechanical and physical properties of the graft (e.g., burst pressure, water entry pressure, suture retention strength). In the preferred manufacturing methodology, the width of the tape 14 is approximately 0.5 inches, irrespective of the number of layers of tape which are to be applied to the base graft 10. Therefore, the pitch (i.e., the distance from leading edge to leading edge of the adjacent convolutions of tape) varies depending on the size of the graft and the numbers of layers of tape desired. For example, when tape having a width of 0.5 inches is used, and a total of five tape layers are desired, the pitch of the tape is 0.1 inches, but if ten layers of tape are desired, the pitch will be 0.05 inches.

Thereafter, a heating apparatus 16, such as an oven, is used to heat the sintered PTFE reinforcement tape 14 and sintered PTFE base graft 10 to a temperature of approximately 355–375° C. for a period of approximately 10–60 minutes to cause the reinforcement tape 14 to become laminated to the outer surface of the tubular base graft 10. This results in the formation of a tape-reinforced tubular graft.

D. Wrapping And Lamination of the External Support Member Onto the Tape-Reinforced Graft Thereafter, while the tape-reinforced tubular graft remains disposed on the rigid mandrel 12, an external reinforcement member 18, preferably a sintered PTFE filament, is helically wound onto the outer surface of the reinforcement tape 14 at a helical disposition which is opposite or substantially different from the helical disposition of the reinforcement tape 14. This may be accomplished by laying the reinforcement member 18 onto the outer surface of the reinforcement tape at a desired angle $A_2$ relative to the longitudinal axis LA of the base graft 10, while concurrently rotating the mandrel in a direction opposite to that used to wrap the reinforcement tape onto the graft 12 and tape-reinforced graft about the longitudinal axis LA. This results in helical wrapping of the external support member 18 onto the outer surface of the reinforcement tape 14 in a helical configuration or pitch which is different from the helical configuration or pitch of the reinforcement tape.

The external support member 18 functions to increase the kink resistance and crush resistance of the graft, without affecting the handling characteristics of the graft. Typically, the helical configuration or pitch of the external support member 18 will remain constant for each size of the graft.

Figure 3:
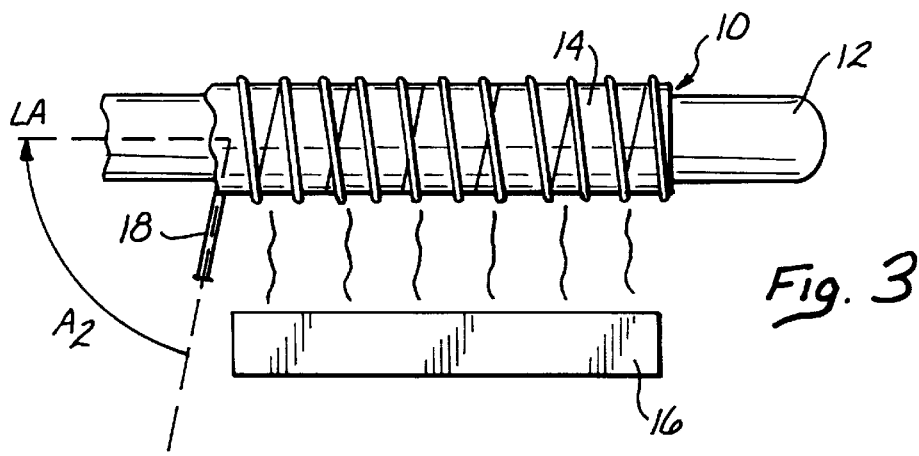
FIG. 3 is an elevational view of a third step in the manufacturing method of the present invention wherein a fluoropolymer filament is helically positioned on, and heat-laminated to, a tape-reinforced tubular graft, the helical disposition of the support filament being in opposite disposition to the helical disposition of the reinforcement tape.
Figure 4:
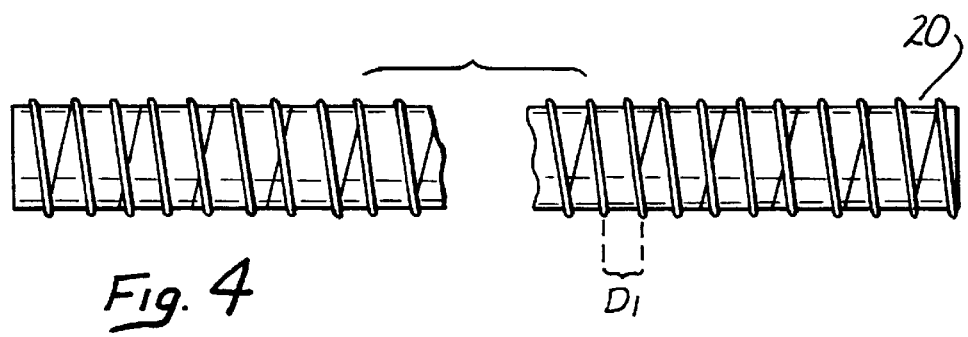
FIG. 4 is an elevational view of a segment of externally supported tape-reinforced tubular vascular graft material manufactured in accordance with the present invention.

In accordance with the present invention, the helical configuration or pitch of the external support member 18 is different from that of the reinforcement tape 14. In some embodiments, such as the embodiment shown in FIGS. 3–4, the size of the angles $A_1$ and $A_2$ at which the tape 14 and reinforcement member 18 are applied to the base graft 12 may be of differing or equivalent size, but the direction of the angles will be opposite one another, thereby resulting in differing helical configurations or pitch of the tape 14 and external support member 18. In other embodiments the directions of the angles $A_1$ and $A_2$ may be the same, but the angular size of such angles $A_1$ and $A_2$ will differ, thereby resulting in directionally similar but different helical configurations or pitches of the reinforcement tape 14 and external support member 18.

After the external support member 18 has been wrapped about the outer surface of the reinforcement tape 14 at its desired helical configuration or pitch, a heating apparatus 16, such as an oven, is used to heat-laminate the external support member 18 to the outer surface of the reinforcement tape 14.

The external reinforcement member 18 may comprise a sintered PTFE monofilament bead, such as the PTFE beading commercially available from Zeus Industrial Products, Inc., Orangeburg, S.C.

The above-described manufacturing method results in the formation of an externally supported tape-reinforced tubular prosthetic graft 20 which comprises a sintered PTFE tubular base graft 10 having a sintered PTFE reinforcement tape 14 helically wrapped thereon in a first helical disposition, and a sintered PTFE reinforcement member 18 helically wrapped on the outer surface of the reinforcement tape 14 in a second helical disposition which is different from the helical disposition of the reinforcement tape 14.

It will be appreciated that the present invention has been described herein with reference to certain preferred or exemplary embodiments and manufacturing methods. The preferred or exemplary embodiments and manufacturing methods described herein may be modified, changed, added to or deviated from without departing from the intended spirit and scope of the present invention, and it is intended that all such additions, modifications, amendments and/or deviations be included within the scope of the following claims.

What is claimed is:

1. A method of manufacturing an externally-supported, tape-reinforced, tubular prosthetic graft, said method comprising the steps of:

a) providing a tubular base graft formed of expanded, sintered fluoropolymer material, said tubular base graft having an inner luminal surface and an outer surface, wherein the tubular base graft is manufactured by a method comprising the following steps;
      i) preparing a fluoropolymer paste by mixing crystalline fluoropolymer powder with a quantity of liquid lubricant;
      ii) forming the fluoropolymer paste into a tubular workpiece;
      iii) expanding the tubular workpiece in at least one axis of expansion;
      iv) drying the tubular workpiece to remove the liquid lubricant therefrom; and
      v) sintering the tubular workpiece to form said tubular base graft;
   b) providing at least one strip of reinforcement tape formed of expanded, sintered fluoropolymer film;
   c) wrapping said reinforcement tape helically around the outer surface of the tubular base graft in a first helical pitch;
   d) causing the helically wrapped reinforcement tape to become attached to the tubular base graft;
   e) providing an external support member formed of substantially non-elastic beading;
   f) helically wrapping the external support member around the helically wrapped reinforcement tape in a second helical pitch which differs from said first helical pitch; and,
   g) causing the helically wrapped external support member to become attached to the helically wrapped reinforcement tape.

2. The method of claim 1 wherein step b) comprises manufacturing a quantity of expanded, sintered fluoropolymer tape by a method comprising the steps of:
   preparing a fluoropolymer paste by mixing a crystalline fluoropolymer powder with a quantity of liquid lubricant;
   forming the fluoropolymer paste into a film;
   calendaring the film;
   drying the film to remove the liquid lubricant therefrom;
   expanding the film in at least one axis of expansion;
   sintering the expanded film; and,
   cutting the expanded, sintered film into strips to thereby form said reinforcement tape.

3. The method of claim 1 wherein step c) comprises:
   laying the reinforcement tape against the outer surface of the tubular base graft at a predetermined angle relative to the longitudinal axis of the tubular base graft and concurrently rotating the tubular base graft about its longitudinal axis so as to helically wrap said reinforcement tape around the outer surface of the tubular base graft in a helical pitch.

4. The method of claim 1 wherein step d) comprises heating the helically wrapped reinforcement tape and tubular base graft to cause the reinforcement tape to become laminated to the base graft.

5. The method of claim 1 wherein step e) comprises:
   providing a quantity of PTFE beading.

6. The method of claim 1 wherein step f) comprises:
   laying the external support member against the outer surface of the reinforcement tape-wrapped tubular base graft at a second predetermined angle relative to the longitudinal axis of the tubular base graft and concurrently rotating the tubular base graft about its longitudinal axis thereby causing the external support member to become helically wrapped around the reinforcement tape in a second helical pitch which differs from the first helical pitch at which the reinforcement tape was wrapped.

7. The method of claim 1 wherein step g) comprises heating the external support member and the reinforcement tape to a temperature which causes the external support member to become laminated to the reinforcement tape.

8. The method of claim 1 wherein:
   step c) comprises laying the reinforcement tape against the outer surface of the tubular base graft at a first predetermined angle relative to the longitudinal axis of the tubular base graft and rotating the tubular base graft about its longitudinal axis so as to helically wrap said reinforcement tape around the outer surface of the tubular base graft in a first helical pitch; and,
   wherein step f) comprises:
      laying the external support member against the outer surface of the reinforcement tape-wrapped tubular base graft at a second predetermined angle relative to the longitudinal axis of the tubular base graft and concurrently rotating the tape-wrapped tubular base graft about its longitudinal axis thereby causing the external support member to become helically wrapped about the reinforcement tape in a second helical pitch which differs from said first helical pitch at which the reinforcement tape was wrapped.

9. The method of claim 8 wherein said first and second predetermined angles are of the same number of degrees relative to the longitudinal axis, but are in different directions relative to the longitudinal axis, thereby resulting in a directional difference between said first helical pitch and said second helical pitch.

10. The method of claim 8 wherein said first and second pre-determined angles are of differing angular size relative to the longitudinal axis of said base graft, thereby resulting in differences in the first helical pitch of the reinforcement tape and the second helical pitch of the external support member.

11. A method of manufacturing an externally-supported, tape-reinforced, tubular prosthetic graft, said method comprising the steps of:

a) providing a tubular base graft formed of expanded, sintered fluoropolymer material, said tubular base graft having an inner luminal surface and an outer surface;
   b) providing at least one strip of reinforcement tape formed of expanded, sintered fluoropolymer film, the tape being provided by manufacturing a quantity of expanded, sintered fluoropolymer tape by a method comprising the steps of:
      i) preparing a fluoropolymer paste by mixing a crystalline fluoropolymer powder with a quantity of liquid lubricant;

ii) forming the fluoropolymer paste into a film;
iii) calendaring the film;
iv) drying the film to remove the liquid lubricant therefrom;
v) expanding the film in at least one axis of expansion;
vi) sintering the expanded film; and,
vii) cutting the expanded, sintered film into strips to thereby form said reinforcement tape c) wrapping said reinforcement tape helically around the outer surface of the tubular base graft in a first helical pitch;

d) causing the helically wrapped reinforcement tape to become attached to the tubular base graft;

e) providing an external support member formed of substantially non-elastic beading;

f) helically wrapping the external support member around the helically wrapped reinforcement tape in a second helical pitch which differs from said first helical pitch; and, g) causing the helically wrapped external support member to become attached to the helically wrapped reinforcement tape.

12. The method of claim 11 wherein step c) comprises:
laying the reinforcement tape against the outer surface of the tubular base graft at a predetermined angle relative to the longitudinal axis of the tubular base graft and concurrently rotating the tubular base graft about its longitudinal axis so as to helically wrap said reinforcement tape around the outer surface of the tubular base graft in a helical pitch.

13. The method of claim 11 wherein step d) comprises heating the helically wrapped reinforcement tape and tubular base graft to cause the reinforcement tape to become laminated to the base graft.

14. The method of claim 11 wherein step e) comprises: providing a quantity of PTFE beading.

15. The method of claim 11 wherein step f) comprises:
laying the external support member against the outer surface of the reinforcement tape-wrapped tubular base graft at a second predetermined angle relative to the longitudinal axis of the tubular base graft and concurrently rotating the tubular base graft about its longitudinal axis thereby causing the external support member to become helically wrapped around the reinforcement tape in a second helical pitch which differs from the first helical pitch at which the reinforcement tape was wrapped.

16. The method of claim 11 wherein step g) comprises heating the external support member and the reinforcement tape to a temperature which causes the external support member to become laminated to the reinforcement tape.

17. The method of claim 11 wherein:
step c) comprises laying the reinforcement tape against the outer surface of the tubular base graft at a first predetermined angle relative to the longitudinal axis of the tubular base graft and rotating the tubular base graft about its longitudinal axis so as to helically wrap said reinforcement tape around the outer surface of the tubular base graft in a first helical pitch; and,
step f) comprises laying the external support member against the outer surface of the reinforcement tape-wrapped tubular base graft at a second predetermined angle relative to the longitudinal axis of the tubular base graft and concurrently rotating the tape-wrapped tubular base graft about its longitudinal axis thereby causing the external support member to become helically wrapped about the reinforcement tape in a second helical pitch which differs from said first helical pitch at which the reinforcement tape was wrapped.

18. The method of claim 17 wherein said first and second predetermined angles are of the same number of degrees relative to the longitudinal axis, but are in different directions relative to the longitudinal axis, thereby resulting in a directional difference between said first helical pitch and said second helical pitch.

19. The method of claim 17 wherein said first and second pre-determined angles are of differing angular size relative to the longitudinal axis of said base graft, thereby resulting in differences in the first helical pitch of the reinforcement tape and the second helical pitch of the external support member.

20. A method of manufacturing an externally-supported, tape-reinforced, tubular prosthetic graft, said method comprising the steps of:

a) providing a tubular base graft formed of expanded, sintered fluoropolymer material, said tubular base graft having an inner luminal surface and an outer surface;

b) providing at least one strip of reinforcement tape formed of expanded, sintered fluoropolymer film;

c) wrapping said reinforcement tape helically around the outer surface of the tubular base graft in a first helical pitch;

d) heating the helically wrapped reinforcement tape and tubular base graft to cause the reinforcement tape to become laminated to the tubular base graft;

e) providing an external support member formed of substantially non-elastic beading;

f) helically wrapping the external support member around the helically wrapped reinforcement tape in a second helical pitch which differs from said first helical pitch; and, g) causing the helically wrapped external support member to become attached to the helically wrapped reinforcement tape.

21. The method of claim 20 wherein step c) comprises:
laying the reinforcement tape against the outer surface of the tubular base graft at a predetermined angle relative to the longitudinal axis of the tubular base graft and concurrently rotating the tubular base graft about its longitudinal axis so as to helically wrap said reinforcement tape around the outer surface of the tubular base graft in a helical pitch.

22. The method of claim 20 wherein step e) comprises: providing a quantity of PTFE beading.

23. The method of claim 20 wherein step f) comprises:
laying the external support member against the outer surface of the reinforcement tape-wrapped tubular base graft at a second predetermined angle relative to the longitudinal axis of the tubular base graft and concurrently rotating the tubular base graft about its longitudinal axis thereby causing the external support member to become helically wrapped around the reinforcement tape in a second helical pitch which differs from the first helical pitch at which the reinforcement tape was wrapped.

24. The method of claim 20 wherein step g) comprises heating the external support member and the reinforcement tape to a temperature which causes the external support member to become laminated to the reinforcement tape.

25. The method of claim 20 wherein:
step c) comprises laying the reinforcement tape against the outer surface of the tubular base graft at a first predetermined angle relative to the longitudinal axis of the tubular base graft and rotating the tubular base graft about its longitudinal axis so as to helically wrap said reinforcement tape around the outer surface of the tubular base graft in a first helical pitch; and, step f) comprises laying the external support member against the outer surface of the reinforcement tape-wrapped tubular base graft at a second predetermined angle relative to the longitudinal axis of the tubular base graft and concurrently rotating the tape-wrapped tubular base graft about its longitudinal axis thereby causing the external support member to become helically wrapped about the reinforcement tape in a second helical pitch which differs from said first helical pitch at which the reinforcement tape was wrapped.

26. The method of claim 25 wherein said first and second predetermined angles are of the same number of degrees relative to the longitudinal axis, but are in different directions relative to the longitudinal axis, thereby resulting in a directional difference between said first helical pitch and said second helical pitch.

27. The method of claim 25 wherein said first and second pre-determined angles are of differing angular size relative to the longitudinal axis of said base graft, thereby resulting in differences in the first helical pitch of the reinforcement tape and the second helical pitch of the external support member.

28. A method of manufacturing an externally-supported, tape-reinforced, tubular prosthetic graft, said method comprising the steps of:

a) providing a tubular base graft formed of expanded, sintered fluoropolymer material, said tubular base graft having an inner luminal surface and an outer surface;

b) providing at least one strip of reinforcement tape formed of expanded, sintered fluoropolymer film;

c) wrapping said reinforcement tape helically around the outer surface of the tubular base graft in a first helical pitch;

d) causing the helically wrapped reinforcement tape to become attached to the tubular base graft;

e) providing an external support member formed of substantially non-elastic beading;

f) helically wrapping the external support member around the helically wrapped reinforcement tape in a second helical pitch which differs from said first helical pitch; and, g) heating the external support member and the reinforcement tape to a temperature which causes the external support member to become laminated to the reinforcement tape.

29. The method of claim 28 wherein step c) comprises:

laying the reinforcement tape against the outer surface of the tubular base graft at a predetermined angle relative to the longitudinal axis of the tubular base graft and concurrently rotating the tubular base graft about its longitudinal axis so as to helically wrap said reinforcement tape around the outer surface of the tubular base graft in a helical pitch.

30. The method of claim 28 wherein step e) comprises:

providing a quantity of PTFE beading.

31. The method of claim 28 wherein step f) comprises:

laying the external support member against the outer surface of the reinforcement tape-wrapped tubular base graft at a second predetermined angle relative to the longitudinal axis of the tubular base graft and concurrently rotating the tubular base graft about its longitudinal axis thereby causing the external support member to become helically wrapped around the reinforcement tape in a second helical pitch which differs from the first helical pitch at which the reinforcement tape was wrapped.

32. The method of claim 28 wherein:

step c) comprises laying the reinforcement tape against the outer surface of the tubular base graft at a first predetermined angle relative to the longitudinal axis of the tubular base graft and rotating the tubular base graft about its longitudinal axis so as to helically wrap said reinforcement tape around the outer surface of the tubular base graft in a first helical pitch; and, step f) comprises laying the external support member against the outer surface of the reinforcement tape-wrapped tubular base graft at a second predetermined angle relative to the longitudinal axis of the tubular base graft and concurrently rotating the tape-wrapped tubular base graft about its longitudinal axis thereby causing the external support member to become helically wrapped about the reinforcement tape in a second helical pitch which differs from said first helical pitch at which the reinforcement tape was wrapped.

33. The method of claim 32 wherein said first and second predetermined angles are of the same number of degrees relative to the longitudinal axis, but are in different directions relative to the longitudinal axis, thereby resulting in a directional difference between said first helical pitch and said second helical pitch.

34. The method of claim 32 wherein said first and second pre-determined angles are of differing angular size relative to the longitudinal axis of said base graft, thereby resulting in differences in the first helical pitch of the reinforcement tape and the second helical pitch of the external support member.

* * * * *